United States Patent
Fasasi et al.

(10) Patent No.: US 11,557,376 B2
(45) Date of Patent: Jan. 17, 2023

(54) RAPID ASSESSMENT OF CRUDE OIL FOULING PROPENSITY TO PREVENT REFINERY FOULING

(71) Applicant: PHILLIPS 66 COMPANY, Houston, TX (US)

(72) Inventors: Ayuba Fasasi, Bartlesville, OK (US); Jinfeng Lai, Bartlesville, OK (US); David A. Henning, Bartlesville, OK (US); Franklin Uba, Bartlesville, OK (US)

(73) Assignee: Phillips 66 Company, Houston, TX (US)

(*) Notice: Subject to any disclaimer, the term of this patent is extended or adjusted under 35 U.S.C. 154(b) by 0 days.

(21) Appl. No.: 17/443,648

(22) Filed: Jul. 27, 2021

(65) Prior Publication Data

US 2022/0028495 A1   Jan. 27, 2022

Related U.S. Application Data

(60) Provisional application No. 63/056,987, filed on Jul. 27, 2020.

(51) Int. Cl.
| | |
|---|---|
| *G16B 40/00* | (2019.01) |
| *C10G 75/00* | (2006.01) |
| *G01N 21/359* | (2014.01) |
| *G01N 24/08* | (2006.01) |
| *G01N 33/28* | (2006.01) |
| *G01N 21/3577* | (2014.01) |

(52) U.S. Cl.
CPC ........... *G16B 40/00* (2019.02); *C10G 75/00* (2013.01); *G01N 21/359* (2013.01); *G01N 21/3577* (2013.01); *G01N 24/081* (2013.01); *G01N 24/085* (2013.01); *G01N 33/2823* (2013.01); *C10G 2300/4075* (2013.01)

(58) Field of Classification Search
None
See application file for complete search history.

(56) References Cited

U.S. PATENT DOCUMENTS

| | | | |
|---|---|---|---|
| 2021/0254792 A1* | 8/2021 | Rady | F17D 3/01 |
| 2021/0254793 A1* | 8/2021 | Rady | F17D 3/05 |
| 2021/0254794 A1* | 8/2021 | Rady | G05D 21/02 |
| 2021/0270426 A1* | 9/2021 | Rady | G01N 33/2823 |
| 2021/0270795 A1* | 9/2021 | Rady | F17D 3/05 |
| 2021/0270796 A1* | 9/2021 | Rady | F17D 3/01 |

* cited by examiner

*Primary Examiner* — Tam M Nguyen
(74) *Attorney, Agent, or Firm* — Phillips 66 Company

(57) ABSTRACT

A process for producing liquid transportation fuels in a petroleum refinery while avoiding the usage of crude oil feed stock that characterized by a fouling thermal resistance having the potential to foul refinery processes and equipment. Spectral data selected from NIR, NMR or both is obtained and converted to wavelets coefficients data. A genetic algorithm (or support vector machines) is then trained to recognize subtle features in the wavelet coefficients data to allow classification of crude samples into one of two groups based on fouling potential. Rapid classification of a potential crude oil feed stock according to its fouling potential prevents the utilization of feed stocks characterized by increased fouling potential in a petroleum refinery to produce liquid transportation fuels.

11 Claims, 9 Drawing Sheets

RAPID ASSESSMENT OF CRUDE OIL FOULING PROPENSITY TO PREVENT REFINERY FOULING

CROSS-REFERENCE TO RELATED APPLICATIONS

This application is a non-provisional application which claims the benefit of and priority to U.S. Provisional Application Ser. No. 63/056,987 filed Jul. 27, 2020, entitled "Rapid Assessment of Crude Oil Fouling Propensity to Prevent Refinery Fouling," which is hereby incorporated by reference in its entirety.

STATEMENT REGARDING FEDERALLY SPONSORED RESEARCH OR DEVELOPMENT

None.

FIELD OF THE INVENTION

The present invention relates to a processes and systems that rapidly determine the propensity of a given crude oil sample to foul refinery process equipment.

BACKGROUND

In a commercial refinery, fouling negatively impacts operations by impeding flow through piping and reducing the efficiency of heat transfer in heat exchangers and the atmospheric distillation unit. It increases energy usage, refinery downtime and maintenance costs. Operational expenditures increase due to decreased overall process efficiency and the increased time required to de-coke process equipment. Refiners have long sought a rapid process that can predict the fouling propensity of a given crude feedstock in order to minimize fouling.

Current conventional procedures for determining the fouling propensity of a given crude oil sample require experimental assays that may take up to several months to complete, which is generally unacceptable in a commercial refinery that may process hundreds of thousands of barrels of oil per day. What is needed is an assay that can rapidly determine fouling propensity of a given crude oil feed stock in minutes and can be implemented at reasonable cost.

BRIEF SUMMARY OF THE DISCLOSURE

Certain embodiments of the inventive process comprise a process for producing a liquid transportation fuel in a commercial petroleum refinery while utilizing only non-fouling crude oil feed stock, comprising: a) analyzing a sample of a crude oil feed stock comprising unrefined petroleum by a spectroscopy method selected from at least one of near-infrared spectroscopy and nuclear magnetic resonance spectroscopy to produce spectral data comprising discrete digitized data points and transforming the spectral data to produce a sample wavelet coefficients data according to wavelet theory by applying a mother wavelet consisting of a member of the Symlet family of mother wavelets, at the third level of decomposition or greater; b) training a genetic algorithm to classify the sample into one of two groups selected from a first group and a second group to produce a trained genetic algorithm, where the first group comprises multiple aliquots comprising crude petroleum that are each of distinct geologic origin and that are each characterized by a fouling thermal resistance of less than 0.002 hr-sq.ft.-F/per British Thermal Unit, where the second group comprises multiple aliquots comprising crude petroleum that are each of distinct geologic origin and that are each characterized by a fouling thermal resistance of at least 0.002 hr-sq.ft.-° F./per British Thermal Unit, where the training comprises performing the analyzing of part a) on each of the aliquots to produce training wavelets coefficients data and presenting the training wavelets coefficients data obtained from each aliquot in the first group and each aliquot in the second group to an untrained genetic algorithm that is instructed to recognize subtle collective differences within the training wavelet coefficients data obtained from aliquots of the first group compared to the training wavelet coefficients data obtained from aliquots of the second group to produce a trained genetic algorithm, where the subtle collective differences represent distinguishing spectral features between the first group and the second group that allow the trained genetic algorithm to classify an aliquot as a member of the first or the second group; c) classifying the sample of a) as a member of either the first group or the second group by presenting the sample wavelets coefficients data of a) to the trained genetic algorithm, where the trained genetic algorithm performs the classifying by examining the data features that collectively predict whether a particular aliquot is a member of the first group or the second group; d) refining the crude oil feed stock comprising unrefined petroleum in a commercial petroleum refinery when the sample of a) is classified as a member of the first group, and not refining the crude oil feed stock comprising unrefined petroleum in a commercial petroleum refinery when the sample of a) is classified as a member of the second group.

In certain embodiments of the process, the classifying identifies the sample of a) as a member of the second group, the crude oil feed stock is diluted by mixing with a quantity of crude oil that is characterized as a member of the first group that is sufficient to decrease the overall fouling thermal resistance of the crude oil feed stock to less than 0.002 hr-sq.ft.-☐F/British Thermal Unit to produce a non-fouling crude oil feed stock and refining the non-fouling crude oil feed stock in a petroleum refinery to produce at least one liquid transportation fuel.

In certain embodiments of the process, the spectroscopy method comprises near-infrared spectroscopy in the range from 3100 cm-1 to 6000 cm-1.

In certain embodiments of the process, the spectroscopy method comprises nuclear magnetic resonance spectroscopy method selected from 1H nuclear magnetic resonance spectroscopy and 13C nuclear magnetic resonance spectroscopy.

In certain embodiments of the process, the mother wavelet is selected from the Symlet4 and Symlet6 mother wavelets. In certain embodiments of the process, the mother wavelet is applied at the fourth level of decomposition. In certain embodiments of the process, the mother wavelet is applied at the fifth level of decomposition.

Certain embodiments of the process additionally comprise curating the potential data features of b) to produce a subset of potential data features that are utilized by the trained genetic algorithm to perform the classifying of c).

In certain embodiments of the process, the spectral data comprises from 50 to 5000 discrete digitized data points.

In certain embodiments of the process, the training of part b) comprises training support vector machines rather than a genetic algorithm to produce trained support vector machines.

In certain embodiments of the process, the classifying of c) comprises presenting the sample wavelets coefficients data of a) to the trained support vector machines.

BRIEF DESCRIPTION OF THE DRAWINGS

A more complete understanding of the present invention and its benefits may be acquired by referring to the description provided herein and the accompanying drawings, where.

Figure 1:
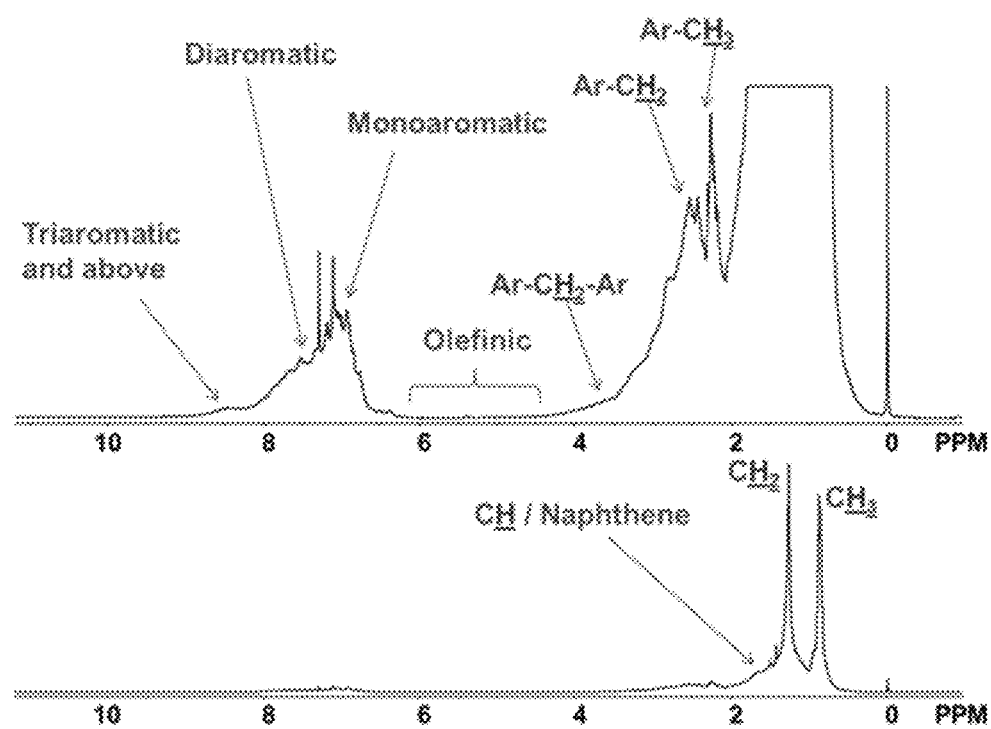
FIG. 1 depicts a typical representative $^1$H NMR spectrum for one sample comprising crude oil (lower panel), and a view of the same spectrum with the Y-axis amplified (upper panel).

The invention is susceptible to various modifications and alternative forms, specific embodiments thereof are shown by way of example in the drawings. The drawings may not be to scale. It should be understood that the drawings are not intended to limit the scope of the invention to the particular embodiment illustrated.

DETAILED DESCRIPTION

Currently utilized models for predicting the fouling propensity of a given sample of crude oil requires crude assay information that can only be obtained by analytical assays that take six hours or more to complete. This greatly hampers the rapid identification of crude oil samples that are capable of fouling process equipment in a commercial refinery setting, leading to potentially increased operating costs.

We sought to develop assays that could rapidly identify the fouling propensity of a given crude oil sample by developing a model that is based upon the near-infrared (NIR) spectral data, the nuclear magnetic resonance (NMR) spectra, or both, for a given crude oil sample. The inventive processes and systems disclosed herein successfully distinguish a specific property of a crude oil sample (i.e., the fouling propensity) based solely upon analysis of specific features obtained from this spectral data. This represents a significant advance in rapidly identifying favorable crudes for use in a commercial petroleum refinery setting.

The inventive process utilizes spectral data obtained from at least one of near infrared spectroscopy (NIR) and nuclear magnetic resonance spectroscopy (NMR) because these techniques are capable of being used to capture "chemical fingerprints" of crude oil samples that can be correlated with the fouling tendencies of each sample. More specifically, NIR spectroscopy provides excited vibrational data while NMR spectroscopy provides data on magnetic field induced molecular chemical shifts that are indicative of the overall molecular composition of each crude oil sample. When utilized together, these two types of data help to more easily identify informative spectral differences between fouling and non-fouling crude oil samples. However, while this distinguishing information is buried within the spectra, it has been impossible to identify these differences solely via attempts to interpret the spectral data. Although NIR and NMR have the unique advantages of capturing significant identifying information about a crude oil sample (when compared to data obtained by other analytical assays), the complexity and subtlety of these spectral signals has been an obstacle.

Further, certain embodiments of the present inventive process are the first to successfully combine NIR spectral data and NMR spectral data to train a genetic algorithm to classify samples of crude oil via the judicious application of wavelet theory to transform the spectral data to wavelet coefficients data that is then utilized to train a genetic algorithm. The selection of an unexpectedly advantageous mother wavelet and concatenation of very subtle but informative selected spectral features enabled the success of the present inventive methodology.

The inventive process and system in part comprises mathematical transformation of the spectral data to wavelets to enhance subtle but informative features in the data. According to wavelet theory, a discrete signal such as a spectral data point can be decomposed into "approximation" and "detail" components. Wavelet packet transform (WPT) was applied to de-noise and de-convolute spectra of crude oil samples by decomposing each spectrum into coefficients (wavelet coefficients) that represent the spectrum's constituent frequencies.

Wavelets offer a different approach to removal of noise from multivariate data than other techniques such as Savitzky-Golay filtering or the fast Fourier transform. Wavelets can often enhance subtle but significant spectral features to increase the general discrimination power of the modeling approach. Using wavelets, a new set of basis vectors is developed in a new pattern space that takes advantage of the local characteristics of the data. These new basis vectors are capable of better conveying the information present in the data than axes that are defined by the original measurement variables.

In the present inventive process, spectral signals were "decomposed" by passing each spectrum through low-pass and high-pass scaling filters to produce a low-frequency "detail" coefficient dataset and a high-frequency "approximation" coefficient dataset. The approximation coefficients correspond to the "low-frequency signal" data in the spectra, while the detail coefficients usually correspond to the "noisy signal" portion of the data. The process of decomposition was continued with different scales of the wavelet filter pair in a step-by-step fashion to separate the noisy components from the signal until the necessary level of signal decomposition was achieved. We have found that wavelet coefficients are especially important and preferred (versus raw spectral data) in modeling fouling propensity because the nature of the basis vectors used to characterize the data are conducive to a variety of approaches for improving the quality of the input data for training. In particular, we unexpectedly found that decomposition of the data using the Symlet6 mother wavelet unexpectedly enabled a genetic algorithm to distinguish spectral features in the resulting wavelet coefficients data that enabled classification of crude oil samples into two groups based upon their fouling propensity.

As mentioned, the inventive process comprises first obtaining spectral information for a given sample comprising crude oil. In certain embodiments, NIR spectral data, NMR spectral data, or both are obtained. The presence of numerous signals in the NMR spectrum is beneficial because those signals provide a type of fingerprint of the crude oil sample that provides spectral features that allow discrimination between oil samples capable of fouling versus those that are not. FIG. 1 depicts a typical NMR spectrum of a sample comprising crude oil, which includes a large number of signals attributed to diverse hydrocarbon types and complex molecular structures. The assignments of chemical shift regions to the corresponding molecular structural types are shown in Table 2 (below).

TABLE 2

Assignments of 1H NMR chemical shifts.

| Chemical Shift Region (ppm) | Assignments |
|---|---|
| 0.2-1.0 | aliphatic $CH_3$ |
| 1.0-1.4 | aliphatic $CH_2$ |
| 1.4-2.0 | naphthenics or CH in isoparaffins |
| 2.0-2.4 | $CH_3$ alpha to aromatics |
| 2.4-3.5 | $CH_2$ or CH alpha to aromatics |
| 3.5-4.5 | bridged $CH_2$ in fluorene types |
| 4.5-6.2 | olefins or diolefins |
| 6.2-7.4 | single-ring aromatics |
| 7.4-8.3 | diaromatics |
| 8.3-10.0 | 3-ring polyaromatics and above |

The region spanning 0.2-1.0 ppm corresponds to aliphatic $CH_3$, region 1.0-1.4 ppm is assigned to aliphatic $CH_2$, region 1.4-2.0 ppm is assigned to naphthenics or CH in isoparaffins, region 2.0-2.4 ppm is attributed to $CH_3$ alpha to aromatics, region 2.4-3.5 ppm corresponds to $CH_2$ or CH alpha to aromatics, region 3.5-4.5 ppm is assigned to bridged $CH_2$ in fluorenes, region 4.5-6.2 ppm is due to olefins or diolefins, region 6.2-7.4 ppm is attributed to single-ring aromatics, region 7.4-8.3 ppm corresponds to diaromatics, and region 8.3-10.0 ppm is assigned to polyaromatics with three rings and above.

Certain embodiments may comprise acquiring $^{13}C$ NMR data rather than $^1H$ NMR data. While the specifics may differ with regards to chemical shifts, the general concept is identical to the utilization of $^1H$ NMR data in conjunction with the present inventive processes. One having average skill in the area of NMR spectroscopy would be familiar with the implementation of $^{13}C$ NMR in place of $^1H$ NMR data, and thus, there is no need to disclose this in greater detail herein.

Certain embodiments comprise obtaining near-infrared spectral data for a sample comprising crude oil. Near-infrared spectral data is typically obtained for wavelengths in the range from 3000 to 6000 $cm^{-1}$. Wavelet packet transform is then applied to de-noise and de-convolute the spectral data obtained for crude oil samples by decomposing the spectral data into coefficients (wavelet coefficients) that represent the sample's constituent frequencies. In the present process, each NIR spectrum is represented by a finite number of wavelet coefficients that typically varies from 50-5000. In certain embodiments, the NIR spectrum may be represented by 300-3000 wavelet coefficients, (e.g., 1333).

Wavelets will often enhance subtle but significant spectral features to increase the general discrimination power of the modeling approach. It is important to note that the selection of alternative mother wavelets other than the Symlet for decomposition of the NIR spectral data results in a profoundly decreased ability for a pattern recognition genetic algorithm to classify crude oil samples according to fouling propensity.

Wavelets offer a different approach to removing noise from multivariate data than Savitzky-Golay filtering or the fast Fourier transform. Using wavelets, a new set of basis vectors are developed that take advantage of the local characteristics of the data, and these vectors convey the information present in the data better than axes defined by the original measurement variables (wavelength). Wavelet coefficients provide the coordinates of the samples in this new pattern space. The mother wavelet selected to develop the new basis set is the one that best matches the attributes of the data. This gets around the problem that occurs when an interfering source of variation in the data is correlated to information about the class membership of the samples (for example, fouling and/or non-fouling) as a result of the design of the study or because of accidental correlations between signal and noise.

Figure 2:
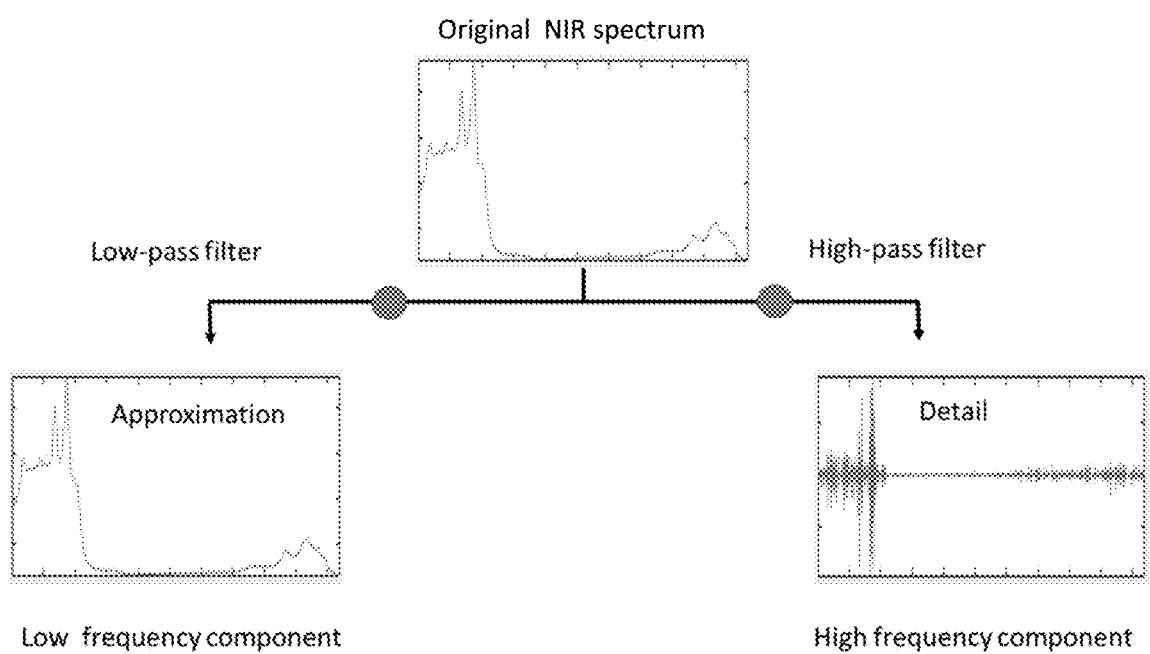
FIG. 2 depicts a diagram demonstrating the decomposition of spectral data according to wavelet theory.
Figure 3:
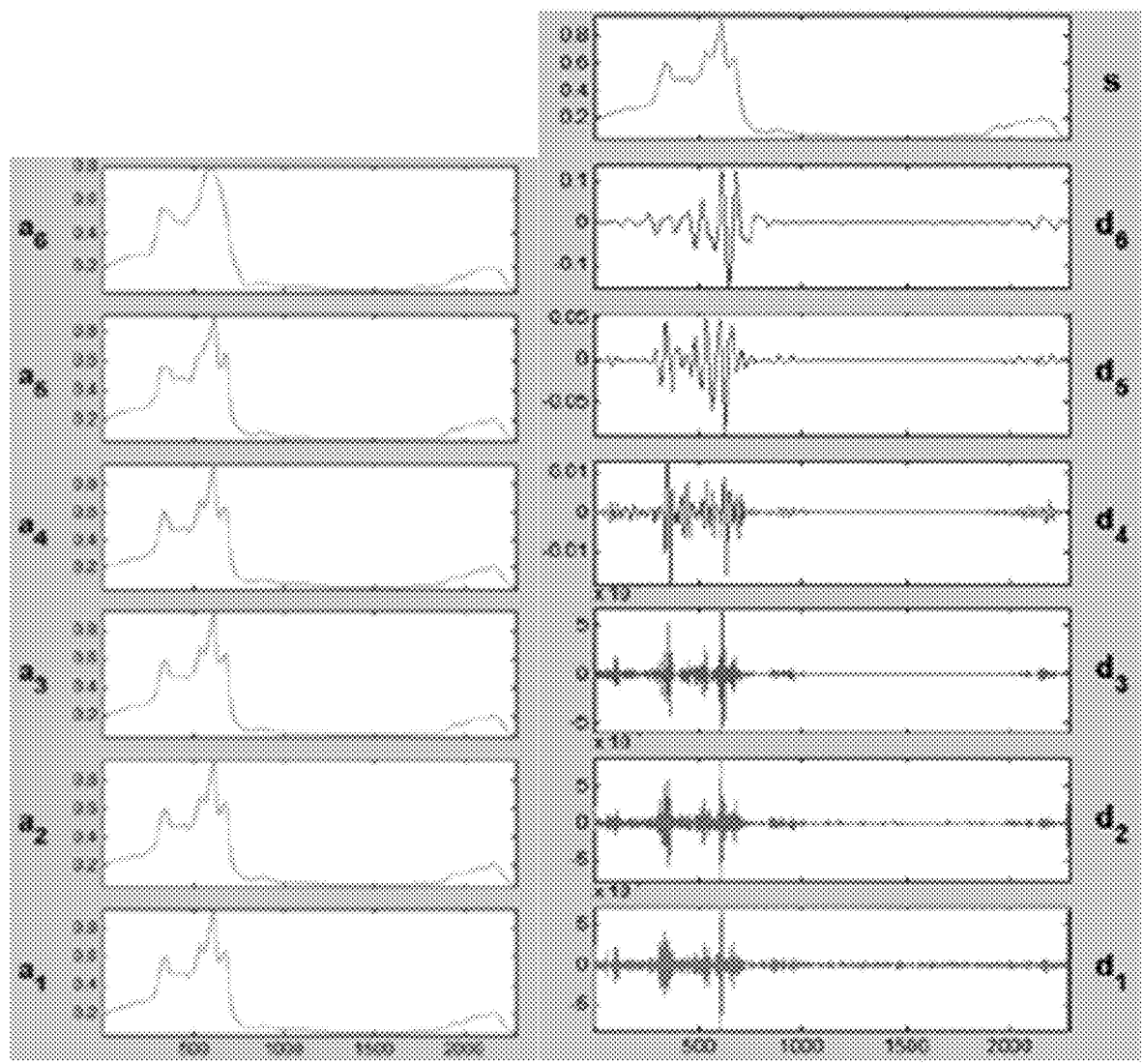
FIG. 3 depicts progressive decomposition of NIR spectral data to produce approximation (a) and detail (d) coefficients data from the first to sixth levels.

Using wavelets, spectral data is decomposed by passing each spectral data point through two scaling filters: a high-pass filter and a low-pass filter (FIG. 2). The low-pass filter allows only the low-frequency component of the signal to be measured as a set of wavelet coefficients, which is called the "approximation." The high-pass filter measures the high-frequency coefficient set, which is called the "detail." The detail coefficients usually correspond to the noisy part of the data. This process of decomposition is continued with different scales of the wavelet filter pair in a step-by-step fashion to separate the noisy components from the signal until the necessary level of signal decomposition has been achieved. FIG. 3 demonstrates an exemplary result utilizing this technique on NIR spectral data (displayed in transmittance mode) obtained from a sample comprising crude oil. FIG. 3 displays the results of wavelet decomposition of the spectral data performed up to the sixth level for the approximation ($a_1$-$a_6$) and detail ($d_1$-$d_6$) components, while "s" indicates the original NIR spectrum.

Wavelet coefficients are especially important and are preferred to raw spectral data for modeling fouling propensity because the nature of the basis vectors used to characterize the data is conducive to a variety of approaches for improving the quality of the data that is used for model training. The wavelet coefficients obtained from each spectrum are organized as a data vector, and each coefficient is auto-scaled. A mother wavelet is selected to develop the new basis set, and historically, certain classes of mother wavelet have been commonly utilized that are considered to be the most effective at extracting distinguishing class information from spectral data. Selecting a mother wavelet to use as a "reference point" helps solve the problem that occurs when an interfering source of variation in the data is correlated to information about the class membership of the samples (e.g. fouling and/or non-fouling) as a result of the design of the study or because of accidental correlations between signal and noise.

During development of the present inventive process it was unexpectedly discovered that the Symlet family of mother wavelets was particularly well-suited to deconvolute and denoise both NIR and NMR spectral data. In fact, applying the Symlet mother wavelet dramatically increased the power of the inventive process to discriminate between fouling and non-fouling crude oil samples. Symlet wavelets are a family of mother wavelets that are modified versions of Daubechies wavelets that are characterized by increased symmetry. Daubechies wavelets are a family of orthogonal wavelets defining a discrete wavelet transform and are characterized by a maximal number of vanishing moments for some given support. With each wavelet type of this class, there is a scaling function (called the father wavelet) which generates an orthogonal multiresolution analysis. Applying the Symlet mother wavelet to analysis and classification of the NIR and NMR spectral data is highly unconventional because conventional practice is to perform mathematical deconvolution of spectral data that is characterized by broad-band signals (e.g., near-infrared spectra) using the "Haar" family of mother wavelets. Conventional wisdom asserts that the Symlet family of mother wavelets should only be applied to decomposition of spectral signals that are characterized by numerous sharp peaks (such as mid-infrared spectral data, or chromatographic data) and that the "Haar" family of mother wavelets is far better-suited for decomposition of NIR or NMR spectral data, which typically do not comprise numerous sharp peaks.

Certain embodiments of the present inventive process utilizes the Symlet4 mother wavelet, while certain alternative embodiments utilize the Symlet6 mother wavelet. The inventive process may apply a Symlet mother wavelet at the third or greater level of decomposition; alternatively, the fourth level of decomposition or greater; alternatively, the fifth level of decomposition. The choice of the Symlet mother wavelet at the third (alternatively, fourth) level of decomposition was found to unexpectedly and fortuitously enhance the rather subtle but informative spectral features in the spectra. This resulted in an improved power of the inventive process to discriminate between fouling and non-fouling crude oil samples. The inventive present process generally comprises training a genetic algorithm or utilizing support vector machines to distinguish between wavelet coefficients data obtained for samples comprising crude oil that are either capable of fouling refinery process equipment versus those that are not. A genetic algorithm is a search heuristic that is inspired by Charles Darwin's theory of natural evolution. This algorithm reflects the process of natural selection where the fittest individuals are selected for reproduction in order to produce offspring of the next generation. The process of natural selection starts with the selection of fittest individuals from a population. They produce offspring which inherit the characteristics of the parents and will be added to the next generation. If parents have better fitness, their offspring will be better than parents and have a better chance at surviving. This process is iterative and eventually results in a generation with the fittest individuals identified. The specifics of training and applying genetic algorithms is familiar to those having experience in the field of data analysis, and thus a more detailed explanation is not provided here.

In certain embodiments of the present inventive process, a genetic algorithm for pattern-recognition analysis is trained to identify distinguishing features within wavelet coefficients data derived from aliquots comprising crude oil, thereby allowing the trained genetic algorithm to classify crude oil samples into two groups depending on their characteristic capacity to foul refinery equipment and processes, or not. In general, a non-fouling crude petroleum sample is characterized by a fouling thermal resistance of less than 0.002 hr-ft$^2$-° F./British Thermal Unit (BTU), while a fouling crude petroleum sample is characterized by a fouling thermal resistance of at least 0.002 hr-ft$^2$-° F./BTU. Even in challenging trials, the present inventive method correctly classified a variety of crude oil samples as either fouling or non-fouling via the identification of selected discriminating features that were developed from wavelet coefficients and identified by a pattern-recognition genetic algorithm.

In certain embodiments, the genetic algorithm is trained using spectral data obtained from five or more aliquots of crude oil having varying fouling thermal resistance characteristics and that are preferably of distinct geologic origin. Certainly, a larger number of distinct aliquots of crude oil is preferred and will result in a trained genetic algorithm that can better discriminate between fouling and non-fouling samples. In certain embodiments, training the genetic algorithm to distinguish between fouling and non-fouling crude petroleum samples may utilize the spectral data obtained from at least 20, at least 35, or at least 50 distinct aliquots of crude oil.

The pattern-recognition genetic algorithm may utilize both supervised learning and unsupervised learning to identify the wavelet coefficients data that corresponds to features (from NIR data) and/or chemical shifts (from NMR data) that facilitate the ability of the genetic algorithm to classify each crude oil sample as either fouling or non-fouling. In embodiments that comprise supervised learning, manual curation to exclude certain data features is performed based upon the probability that such features may have resulted from areas of the spectral data with a low signal to noise ratio. The result of such manual curation is a subset of features (often the two or three largest principal components of the data) that is utilized by the trained genetic algorithm to classify each sample comprising crude oil. Pattern-recognition by the genetic algorithm of spectral feature differences representing the principal components in crude oil samples maximizes the variance between groups (i.e., fouling and non-fouling samples), which also maximizes the percentage of data utilized by the pattern recognition genetic algorithm to classify each sample that is derived from spectral differences between the groups. A principal-component plot that shows separation of the samples into two groups can be generated using only a curated subset of spectral features that provide the most information about the differences between the crude oil samples, simplifying classification along fouling lines. This fitness criterion dramatically reduces the size of the search space because it limits the classification search to a small number of spectral features within the wavelet coefficients data that are capable of distinguishing unknown samples comprising crude oil into one of the two classes.

Further, as the pattern-recognition genetic algorithm trains, it focuses on those samples that are difficult to classify by boosting the relative importance of distinguishing spectral features associated with those samples. Over time, the genetic algorithm learns in a manner similar to how a neural network learns. The pattern-recognition genetic algorithm integrates aspects of artificial intelligence and evolutionary computations to yield the trained genetic algorithm of the present inventive processes and systems.

Certain embodiments utilize support vector machines rather than a trained genetic algorithm to classify crude oil samples as either fouling or non-fouling. Support vector machines (SVM) and neural networks are examples of non-parametric discriminants that operate by attempting to divide a data space into distinct regions. For a binary classifier, the data space is divided into two regions. Samples that share a common property will be found on one side of the decision surface, while those samples classified in the second category will be found on the other side. The present process efficiently divides the data space into two regions: crude oil samples that are characterized as either "fouling" or "non-fouling".

SVM can be used to address classification and regression problems. In classification context, they generate linear boundaries between object groups in a transformed space of the x-variables, which are usually of much higher dimension than the original x-space. The idea of the transformed higher dimensional space is to make groups linearly separable. These class boundaries are constructed in order to maximize the margin between the groups.

Figure 4:
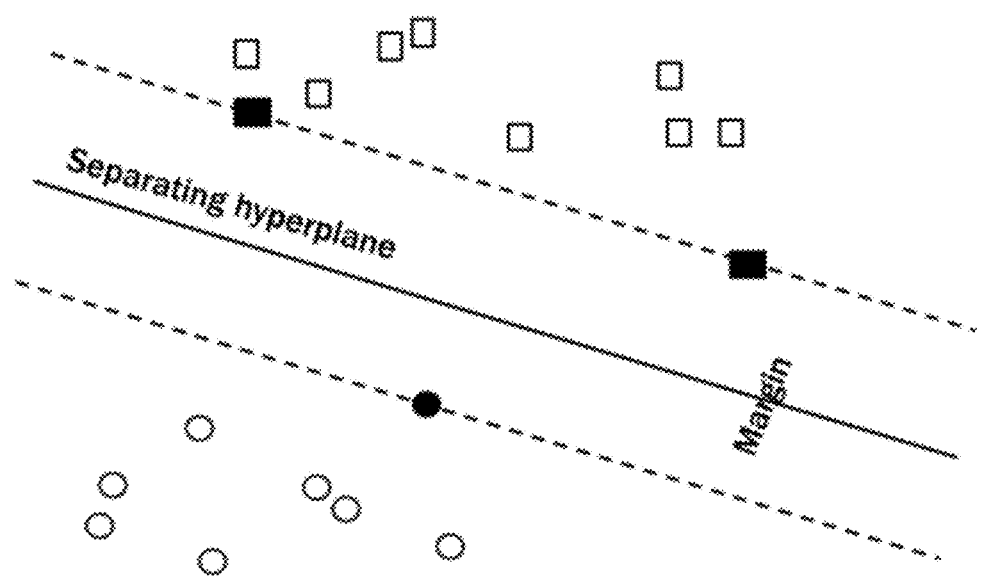
FIG. 4 depicts a plot of samples representing two classes separated by a separating hyperplane that establishes the widest margin to discriminate between the samples belonging to the two different classes.

SVM identifies decision surfaces or hyperplanes that establish the widest margin to discriminate between samples belonging to different classes in a data set. An example hyperplane is shown in FIG. 4, with samples representing one class (circles) on one side of the dividing hyperplane and samples representing a second class on the opposite side of the separating hyperplane. The algorithm uses only some samples in the data set, which are known as support vectors. The input data are mapped from the original measurement space to a higher-dimensional space using kernel functions to simplify the classification problem. There are a variety of kernel functions, including linear kernels for linear hyperplanes as well as polynomial, Gaussian, and sigmoidal kernels for nonlinear decision surfaces. Kernel functions simplify the classification problem by allowing direct computation of the dot product of the weight vector, which defines the distance between the hyperplane and each support vector in the original measurement space. For a linearly separable data set, there will be a large number of linear hyperplanes that can be developed to separate samples into their respective classes. The hyperplane best able to generalize the data (i.e., accurately classify both the training and test sets) is the one with the widest margin. For data sets that are not linearly separable, a nonlinear decision surface will be used (e.g. separating fouling from non-fouling crude oil samples). The kernel function that yields the best classification of the samples is selected for discriminant development. When a classification rule is being developed for a non-separable data set, the optimization problem is reformulated to allow for samples, but as few as possible, to be present in the margin. SVM have some unique advantages. They have good generalization ability because the optimization problem is less prone to over-fitting when the appropriate kernel functions are used. This is because there are fewer model parameters to compute from the data. In addition, SVM are easier to train when compared with conventional methods.

Figure 5:
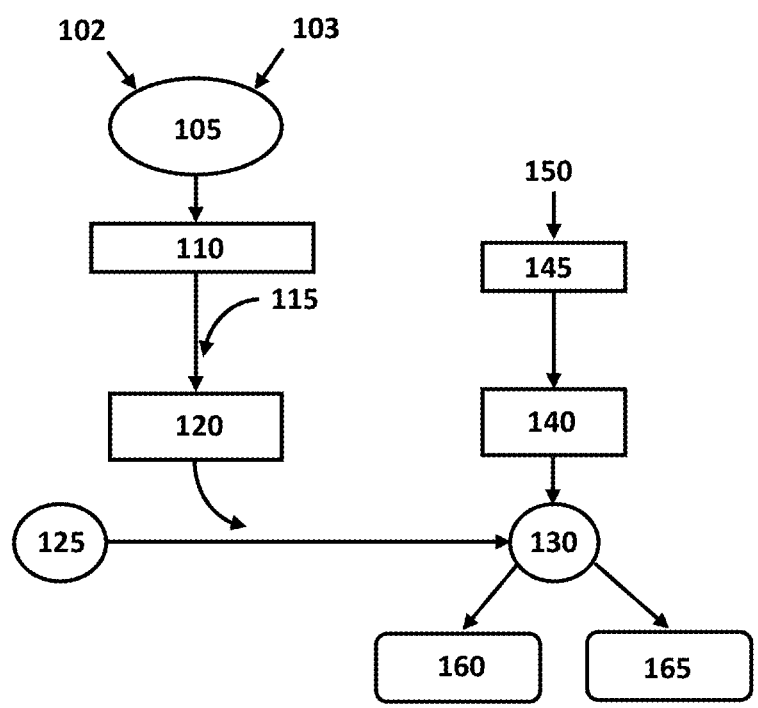
FIG. 5 is a simplified diagram depicting a first embodiment of the present inventive process and system.

A first embodiment of the inventive process and system is illustrated by the flow diagram of FIG. 5. In general terms, the embodiment comprises training a genetic algorithm to recognize subtle collective differences within data obtained from two groups, a first group comprising aliquots of non-fouling crude oil that are each characterized by a fouling thermal resistance of less than 0.002 hr-ft$^2$-° F./BTU and a second group comprising aliquots of crude oil that are each characterized by a fouling thermal resistance of at least 0.002 hr-ft$^2$-° F./BTU and are capable of causing fouling in petroleum refinery processes and equipment.

The training wavelet coefficients data obtained from aliquots of the first group are collectively compared to the training wavelet coefficients data obtained from aliquots of the second group by the genetic algorithm, wherein the genetic algorithm performs an iterative process that eventually distinguishes spectral features that differ between the first group (viewed collectively) and the second group, thereby producing a trained genetic algorithm. The trained genetic algorithm is then capable of quickly classifying a sample of a crude oil feed stock (having an unknown fouling thermal resistance) as a member of the first or the second group.

In the embodiment shown in FIG. 5, multiple aliquots comprising crude petroleum that are collectively referred to as the first group 102 and multiple aliquots comprising crude petroleum that are collectively referred to as the second group 103 are analyzed by a spectral method 105 comprising at least one of NIR and NMR to produce spectral data 110, where the spectral data obtained for each aliquot by spectral method 105 comprises multiple distinct digitized data points. Each of the first group 102 and the second group 103, respectively, comprise at least five aliquots, where each aliquot is preferably of distinct geologic origin from others within the group and in the case of the second group, each aliquot is characterized by a different fouling thermal resistance of at least 0.002 hr-ft$^2$-° F./BTU.

The spectral data 110 for each aliquot is transformed to training wavelet coefficients data 120 according to wavelet theory by processing the data using a mother wavelet 115 that comprises a member of the Symlet family of mother wavelets. In certain embodiments, a member of the Symlet mother wavelet family that is selected from the Symlet4 and Symlet6 mother wavelets. The mother wavelet 115 is utilized to decompose the spectral data 110 to the third level of decomposition or greater to produce training wavelet coefficients data 120. Commercially available computer software (for example, but not limited to, MATLAB®) may be employed to facilitate the iterative decomposition process, but such software is not essential in order to practice the inventive process as described herein.

The embodiment trains a genetic algorithm, which comprises presenting an untrained genetic algorithm 125 that designed to perform data pattern recognition with the training wavelet coefficients data 120 obtained from each of the multiple aliquots comprising the first group 102 and the second group 103, respectively. While training, the untrained genetic algorithm 125 recognizes subtle patterns, or spectral features that are located within the training wavelet coefficients data 120 to produce a trained genetic algorithm 130 that utilizes a the potential differentiating data features to classify a given sample comprising crude oil as either non-fouling or fouling.

The trained genetic algorithm 130 is operable to recognize differentiating data features within sample wavelets coefficients data 140 that is derived from the sample NIR and/or NMR spectral data 145 of an uncharacterized sample 150 comprising crude oil. The trained genetic algorithm 130 then classifies the uncharacterized sample 150 comprising crude oil as a either first group feed stock 160 or a second group feed stock 165 wherein the first group feed stock 160 comprises a non-fouling crude oil sample characterized by a fouling thermal resistance of less than 0.002 hr-ft$^2$-° F./BTU and the second group feed stock 165 comprises a fouling crude oil test sample characterized by a fouling thermal resistance of at least 0.002 hr-ft$^2$-° F./BTU. The uncharacterized sample 150 is analyzed by NIR and/or NMR in a similar (or identical) way as was descried for the multiple aliquots comprising the first group 102 and the second group 103 to acquire the sample NIR and/or NMR spectral data 145. The sample NIR and/or NMR spectral data 145 is converted to sample wavelets coefficients data 140 that is then presented to the trained genetic algorithm 135. The trained genetic algorithm 135 recognizes differentiating data features within the sample wavelets coefficients data 140, which enables the trained genetic algorithm 135 to classify the uncharacterized sample 150 as a member of either the first group 160 or the second group 165.

Certain embodiments comprise manually curating potential differentiating features in the wavelets coefficients data that are identified by the genetic algorithm. This eliminates potential differentiating features with the highest probability of being a false positive (i.e., derived from a region of the spectral data that is characterized by a low signal to noise ratio). A second embodiment of the inventive process and system that includes manual curation of the data is illustrated by the flow diagram of FIG. 6.

The embodiment comprises training a pattern-recognition genetic algorithm to recognize subtle collective differences within data obtained from two groups, a first group comprising aliquots of non-fouling crude oil that are each characterized by a fouling thermal resistance of less than 0.002 hr-ft$^2$-° F./BTU and a second group comprising aliquots of crude oil that are each characterized by a fouling thermal resistance of at least 0.002 hr-ft$^2$-° F./BTU and typically capable of causing fouling in petroleum refinery processes and equipment.

Similar to the first embodiment, the training wavelet coefficients data obtained from aliquots of the first group are collectively compared to the training wavelet coefficients data obtained from aliquots of the second group by the genetic algorithm, wherein the genetic algorithm performs an iterative process that eventually distinguishes spectral features that differ between the first group (viewed collectively) and the second group, thereby producing a trained genetic algorithm. The trained genetic algorithm is then capable of quickly classifying a sample of a crude oil feed stock (having an unknown fouling thermal resistance) as a member of the first or the second group.

Figure 6:
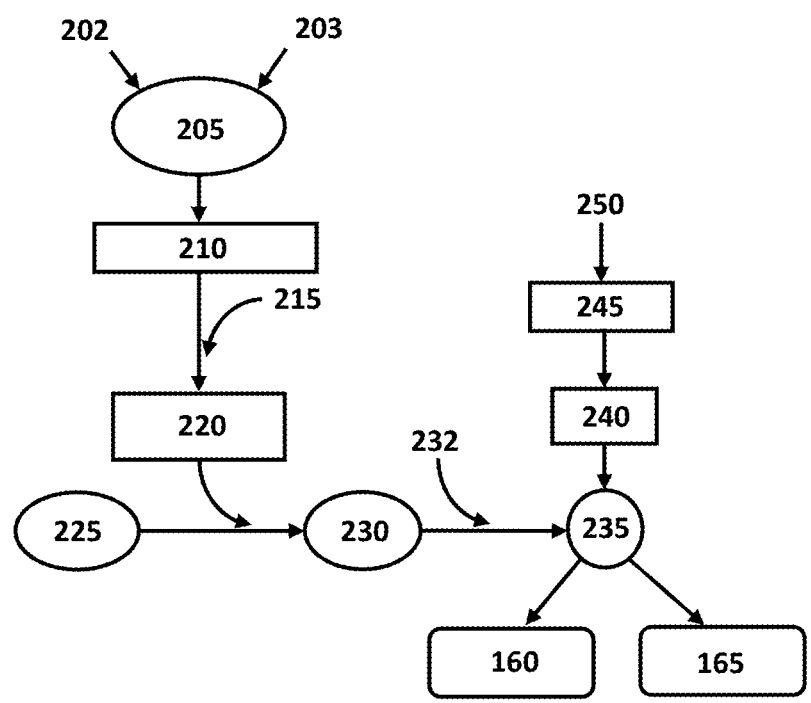
FIG. 6 is a simplified diagram depicting a second embodiment of the present inventive process and system.

In the embodiment shown in FIG. 6, multiple aliquots comprising crude petroleum that are collectively referred to as the first group 202 and multiple aliquots comprising crude petroleum that are collectively referred to as the second group 203 are analyzed by a spectral method 205 comprising at least one of NIR and NMR to produce spectral data 210, where the spectral data obtained for each aliquot by spectral method 205 comprises multiple distinct digitized data points. Each of the first group 202 and the second group 203, respectively, comprise at least five aliquots, where each aliquot is preferably of distinct geologic origin from others within the group and in the case of the second group, each aliquot is characterized by a different fouling thermal resistance of 0.002 hr-ft$^2$-° F./BTU or more.

The spectral data 210 for each aliquot is transformed to training wavelet coefficients data 220 according to wavelet theory by processing the data using a mother wavelet 215 that comprises a member of the Symlet family of mother wavelets. In certain embodiments, a member of the Symlet mother wavelet family that is selected from the Symelet4 and Symlet6 mother wavelets. The mother wavelet 215 is utilized to decompose the spectral data 210 to the third level of decomposition or greater to produce training wavelet coefficients data 220. Commercially available computer software (for example, but not limited to, MATLAB®) may be employed to facilitate the iterative decomposition process, but such software is not essential in order to practice the inventive process as described herein.

The embodiment trains a genetic algorithm, which comprises presenting an untrained genetic algorithm 225 that designed to perform data pattern recognition with the training wavelet coefficients data 220 obtained from each of the multiple aliquots comprising the first group 202 and the second group 203, respectively. While training, the untrained genetic algorithm 225 recognizes subtle patterns, or spectral features that are located within the training wavelet coefficients data 220 to produce a trained genetic algorithm intermediate 230. In the embodiment depicted in FIG. 6, potential differentiating data features that are recognized by the untrained genetic algorithm 225 are then subjected to manual curation 232 to produce a trained genetic algorithm 235 that utilizes a curated subset of the potential differentiating data features to classify a given sample comprising crude oil as either non-fouling or fouling. Manual curation 232 of potential differentiating data features comprises eliminating from consideration any potential differentiating data features recognized by the trained genetic algorithm intermediate 230 that are deemed by either a process operator or an automated curation process to have a high probability of contributing to an inaccurate classification. Potential differentiating data features most likely to be subject to manual curation typically are located in a region of the spectral data where the data is typically characterized by a low signal to noise ratio.

The trained genetic algorithm 235 is characterized by a curated subset of differentiating data features, which makes the trained genetic algorithm 235 operable to recognize differentiating data features within sample wavelets coefficients data 240 that is derived from the NIR and/or NMR spectral data 245 of an uncharacterized sample 250 comprising crude oil. The trained genetic algorithm 235 then classifies the uncharacterized sample 250 comprising crude oil as a either first group feed stock 260 or a second group feed stock 265 wherein a first group feed stock 260 comprises a non-fouling crude oil sample characterized by a fouling thermal resistance of less than 0.002 hr-ft$^2$-° F./BTU and a second group feed stock 265 comprises a fouling crude oil test sample characterized by a fouling thermal resistance of at least 0.002 hr-ft$^2$-° F./BTU. The uncharacterized sample 250 is analyzed by NIR and/or NMR in a similar (or identical) way as was descried for the multiple aliquots comprising the first group 202 and the second group 203 to acquire the NIR and/or NMR spectral data 245. The NIR and/or NMR spectral data 245 is converted to sample wavelets coefficients data 240 that is then presented to the trained genetic algorithm 235. The trained genetic algorithm 235 recognizes differentiating data features within the sample wavelets coefficients data 240, which enables the trained genetic algorithm 235 to classify the uncharacterized sample 250 as a member of either the first group 260 or the second group 265.

The following examples of certain embodiments of the invention are given. Each example is intended to illustrate a specific embodiment, but the scope of the invention is not intended to be limited to the embodiments specifically disclosed. Rather, the scope is intended to be as broad as is supported by the complete disclosure and the appending claims.

Example 1

As a first step toward training a genetic algorithm to distinguish those crude oils having the potential to foul refinery processes, 63 crude oils samples of distinct geologic origin were obtained and their fouling propensity was determined in a conventional manner using a conventional Hot Liquid Process Simulator (HPLS), prior to analyzing the samples by either near-infrared spectroscopy (NIR) or nuclear magnetic resonance spectroscopy (NMR). While an HPLS apparatus may be utilized to measure fouling thermal resistance of crude samples utilized with the present inventive processes, other conventional laboratory tests may also be utilized to measure fouling thermal resistance.

Figure 7:
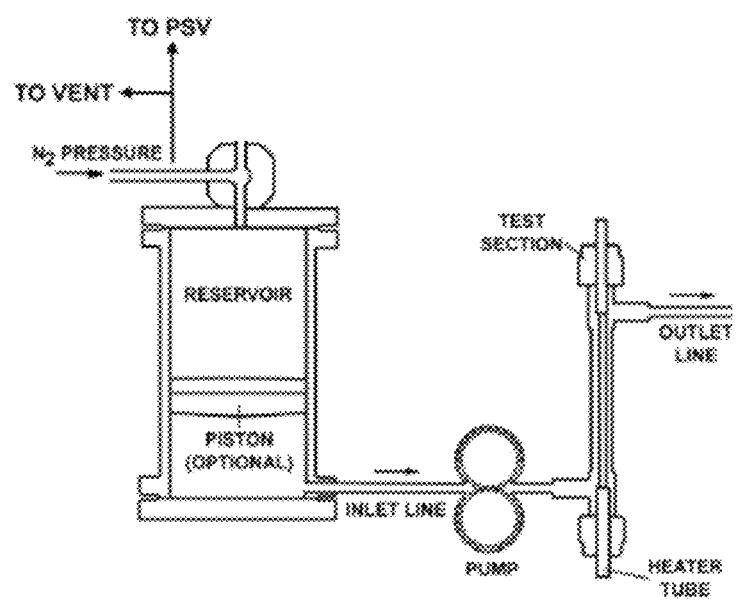
FIG. 7 depicts a simplified diagram of a hot liquid process simulator apparatus.

The general operational layout of a HPLS is diagrammed in FIG. 7. The HPLS pumps a test liquid upward through an annular test section that contains a heated rod made of carbon steel. The heated rod is hollow, with an internally mounted control thermocouple, and the rod is electrically heated to maintain constant temperature. The following test conditions were chosen:

Rod temperature: 698° F. (370° C.)
Rod Metallurgy: Carbon Steel
Liquid feed line and pump temperature: 22° C.
Flow rate: 1 mL/min (no recirculation)
Line pressure: 500 psig As foulants accumulate on the rod, they insulate the rod and reduce the rate of heat transfer to the liquid, thereby causing a decrease over time of the temperature of the test liquid measured at the outlet of the test chamber containing the heated rod. The results are expressed as fouling thermal resistance (FTR) per unit of time (set at 1 hr) per sq. ft. where FTR is equal to the inverse of the heat transfer coefficient (or, 1/U). Thus, $FTR=1/U=A \times \Delta T \div Q$, where Q=heater rod power
U=heat transfer coefficient
A=surface area of the heater rod
$\Delta T$=change in temperature of the rod=$T_{ROD}-(T_{INLET}+T_{OUTLET})/2$ Using the HPLS, FTR values were determined for the 63 different aliquots comprising crude oil feed stocks of distinct geologic origin and obtained from different regions around the world. The resulting FTR values ranged from 0.000 hr-ft$^2$-° F./BTU to 0.00616 hr-ft$^2$-° F./BTU. A crude oil sample characterized by a FTR value below 0.002 hr-ft$^2$-° F./BTU (as measured by the HPLS) were classified as "non-fouling" (Group 1), while a crude oil sample with a fouling thermal resistance that met or exceeded a value of 0.002 hr-ft$^2$-° F./BTU or above was classified as "fouling". All units of thermal fouling resistance in the present disclosure are as measured by the HPLS method, which may not necessarily coincide with actual fouling thermal resistance.

Example 2

From the 63 samples comprising crude oil that were characterized for fouling characteristics in Example 1, approximately 30 aliquots comprising crude oil were chosen that were characterized as "non-fouling" (Group 1) according to the criteria described above, and approximately 30 samples were chosen that were characterized as "non-fouling" (Group 2). The samples were first analyzed by NIR to obtain spectral data comprising more than 1300 discrete digitized data points in the range from 4000 to 6000 cm$^{-1}$. Measurements were carried out on an ABB Bomem FT-NIR spectrometer equipped with a deuterated triglycine sulfate (DTGS) detector. Samples were scanned in a fixed 0.5 mm cell with sapphire windows at a temperature of 90° F. (32.2° C.). The spectral resolution was 4 cm$^{-1}$ and the number of sample scans and background scans was 32, respectively.

The Group 1 and Group 2 samples (described above) were also each analyzed by $^1$H nuclear magnetic resonance spectroscopy (NMR) to obtain NMR spectral data. A representative $^1$H NMR spectrum of a sample comprising crude oil is shown in FIG. 1, and methods for obtaining such spectral data are both described herein, and conventional in nature. They will therefore not be described in further detail here.

The digitized spectral data obtained by both NIR and NMR was then transformed by wavelet packet transform according to wavelet theory to produce wavelet coefficients data. Each spectrum comprising near-infrared spectral data was decomposed according to wavelet theory using a mother wavelet from the Symlet family of mother wavelets. Decomposition comprised passing the spectral data through two scaling filters: a high pass filter and a low pass filter. As mentioned previously, FIG. 2 demonstrates how the high-pass scaling filter allowed only the high-frequency component of the original spectral data to be converted to an "detail coefficient data set", while the low-pass scaling filter allowed only the low-frequency component of the original spectral data to be converted to an "approximation coefficient data set". Commercially available computer software (for example, but not limited to MATLAB®) may be employed to assist in this transformation but is not required in order to practice the inventive process as described herein.

The process of signal decomposition was continued with different scales of the wavelet filter pair in a step-by-step fashion to separate the noisy components from the signal until the appropriate level of signal decomposition was achieved. Applying the Symlet6 mother wavelet, it was determined that the third level of decomposition or greater allowed discrimination of signal from noise. In certain embodiments, the fourth level of decomposition or greater allowed discrimination of signal from noise. A distinct decrease in ability to discriminate signal from noise occurred when non-Symlet mother wavelets were utilized.

The decomposed wavelet coefficient data for each of the 63 crude oil samples were used to train a pattern-recognition genetic algorithm to recognize potential spectral features that might allow the algorithm to distinguish between samples characterized as "fouling" and samples characterized as "non-fouling". Training a pattern-recognition genetic algorithm comprised presenting an untrained genetic algorithm (designed for pattern recognition) with the training wavelet coefficients data obtained from the multiple aliquots representing the first group and the second group, respectively. As the genetic algorithm examined the data and identified potential features in the wavelets coefficients data that could assist in differentiating between the two classes, certain identified potential features were eliminated by manual curation to eliminate identified potential features with the highest probability of being a false positive (i.e., derived from an region of the data that is characterized by a low signal to noise ratio). The process of manual curation can also be thought of as a "search pre-filtering" that pre-screens data that is used by the final trained genetic algorithm to classify samples. Manual curation or pre-filtering served to: 1) decrease the total data to be reviewed by the genetic algorithm when classifying a sample, and 2) assure that potential features that were the result of noise in the data were not utilized by the trained genetic algorithm during classification samples comprising crude oil. The remaining features that were utilized by the trained genetic algorithm for classification typically were associated with spectral features associated with the 2-3 most prevalent classes of chemical components in the sample.

Figure 8:
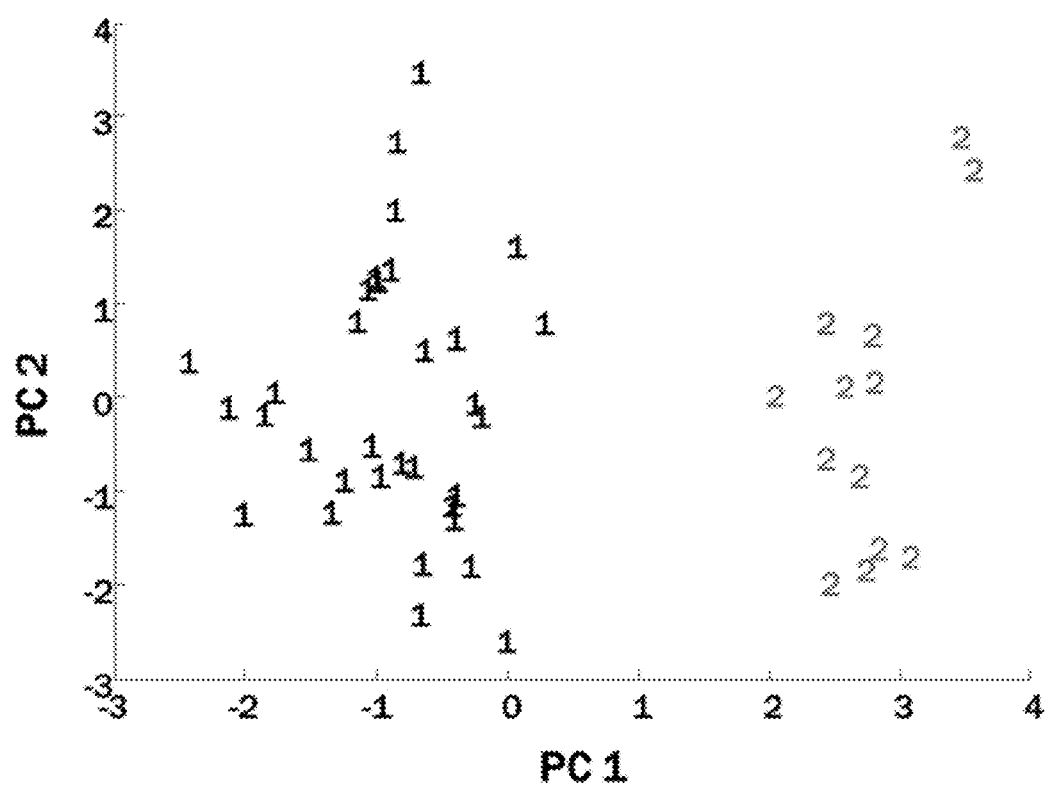
FIG. 8 is a plot of wavelet coefficient data for each of two principle components in crude oil samples that were recognized by pattern recognition genetic algorithm.

One example of classification performed by a trained genetic algorithm is provided in FIG. 8, which depicts wavelet coefficient data for each of two principle components (principle Component 1=PC1; Principle Component 2=PC2) in the training aliquots comprising crude oil, plotted relative to each other. The trained genetic algorithm correctly categorized each aliquot as belonging to either the non-fouling first group (plotted as samples represented by the numeral 1) or the fouling second group (plotted as samples represented by the numeral 2).

Once the pattern recognition genetic algorithm was trained using the various training aliquots the trained genetic algorithm was competent to accurately classify the relative fouling potential of unknown samples comprising crude oil.

Example 3

Figure 9:
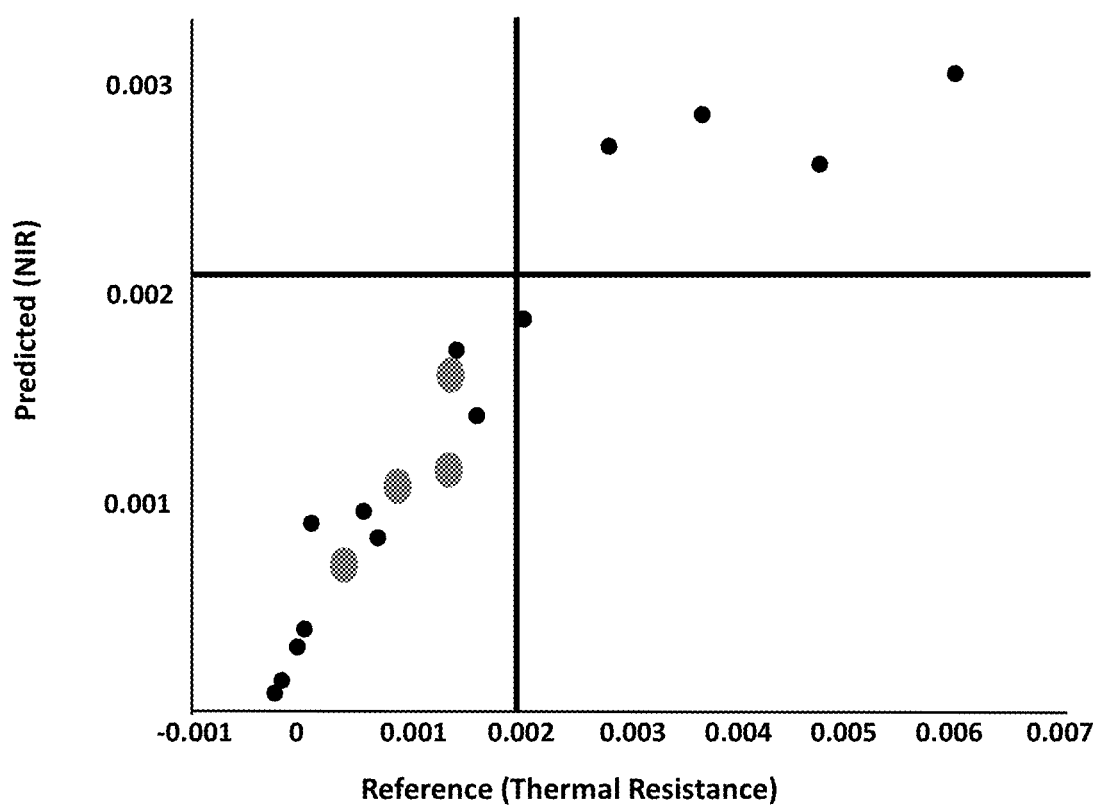
FIG. 9 is a plot representing correlation between the measured fouling thermal resistance (x-axis) for a given training sample versus the fouling thermal resistance predicted by SVM (y-axis).

Certain embodiments utilize support vector machines rather than a genetic algorithm to recognize potential differentiating spectral features in wavelet coefficients data and classify samples comprising crude oil as either fouling or non-fouling. FIG. 9 graphically depicts the strong correlation between measured and predicted fouling potential for a variety of crude oil samples when using SVM to classify samples. The figure plots predicted fouling thermal resistance for a given sample (using support vector machines) versus the actual fouling thermal resistance of the aliquot measured using the HPLS method described in Example 1. The horizontal and vertical lines through the plotted area represent the threshold fouling thermal resistance that would classify a given sample as either non-fouling (Group A in figure) or fouling (Group B in the figure).

Wavelet coefficients data was first obtained from NIR spectral data (as described herein) for various training aliquots comprising either non-fouling (Group A) or fouling (Group B) crude oil. The wavelets coefficients data was analyzed by SVM to generate a best fit hyperplane through the data (see FIG. 4) that would divide the training aliquots into non-fouling (Group A in the figure) and fouling groups (Group B in the figure), thereby producing a trained SVM. Analyzing of samples comprising crude oil by the trained SVM allowed most samples comprising crude oil to be easily classified according to fouling propensity.

In FIG. 9, each plotted point (small circle) represents the correlation between the measured fouling thermal resistance (x-axis) measured by HPLS (as in Example 1) for a given training sample versus the fouling thermal resistance predicted by SVM (y-axis). The good predictive ability of the SVM to accurately classify the training samples is indicated by the observed strong direct correlation for the training data points (small circles). The trained SVM was then utilized to properly classify four unknown samples comprising crude oil (large ovals), which were all determined to fall within Group A (lower left quadrant of the graph) corresponding to "non-fouling" samples and confirmed the predictive ability of the SVM model. Samples in "Group B" would have been classified as "fouling".

Although the systems and processes described herein have been described in detail, various changes, substitutions, and alterations can be made without departing from the spirit and scope of the invention as delineated by the following claims. Further, the description, abstract and drawings are not intended to limit the scope of the claims to the embodiments disclosed.

In the present description, the term fouling refers to deposit formation, encrustation, scaling, scale formation, slagging, and sludge formation in a petroleum refinery setting, which has an adverse effect on operations. It is the accumulation of unwanted material within a refinery processing unit or on solid surfaces of the unit that is detrimental to function. When it does occur during refinery operations, the major effects include (1) loss of heat transfer as indicated by charge outlet temperature decrease and pressure drop increase, (2) blocked process pipes, (3) under-deposit corrosion and pollution, and (4) localized hot spots in reactors and furnace tubes, all of which lead to production losses and increased maintenance costs.

We claim:

1. A process for producing a liquid transportation fuel in a commercial petroleum refinery, comprising:
    a) analyzing a sample of a crude oil feed stock comprising unrefined petroleum by a spectroscopy method selected from at least one of near-infrared spectroscopy and nuclear magnetic resonance spectroscopy to produce spectral data comprising discrete digitized data points and transforming the spectral data to produce a sample wavelet coefficients data according to wavelet theory by applying a mother wavelet consisting of a member of the Symlet family of mother wavelets, at the third level of decomposition or greater;
    b) training a genetic algorithm to classify the sample into one of two groups selected from a first group and a second group to produce a trained genetic algorithm,
        wherein the first group comprises multiple aliquots comprising crude petroleum that are each of distinct geologic origin and that are each characterized by a fouling thermal resistance of less than 0.002 hr-sq.ft.-° F./per British Thermal Unit,
        wherein the second group comprises multiple aliquots comprising crude petroleum that are each of distinct geologic origin and that are each characterized by a fouling thermal resistance of at least 0.002 hr-sq.ft.-° F./per British Thermal Unit,
        wherein the training comprises performing the analyzing of part a) on each of the aliquots to produce training wavelets coefficients data and presenting the training wavelets coefficients data obtained from each aliquot in the first group and each aliquot in the second group to an untrained genetic algorithm that is instructed to recognize subtle collective differences within the training wavelet coefficients data obtained from aliquots of the first group compared to the training wavelet coefficients data obtained from aliquots of the second group to produce a trained genetic algorithm, wherein the subtle collective differences represent distinguishing spectral features between the first group and the second group that allow the trained genetic algorithm to classify an aliquot as a member of the first or the second group;
    c) classifying the sample of a) as a member of either the first group or the second group by presenting the sample wavelets coefficients data of a) to the trained genetic algorithm, wherein the trained genetic algorithm performs the classifying by examining the data features that collectively predict whether a particular aliquot is a member of the first group or the second group;
    d) refining the crude oil feed stock comprising unrefined petroleum in a commercial petroleum refinery when the sample of a) is classified as a member of the first group, and not refining the crude oil feed stock comprising unrefined petroleum in a commercial petroleum refinery when the sample of a) is classified as a member of the second group.

2. The process of claim 1, wherein when the classifying identifies the sample of a) as a member of the second group, the crude oil feed stock is diluted by mixing with a quantity of crude oil that is characterized as a member of the first group that is sufficient to decrease the overall fouling thermal resistance of the crude oil feed stock to less than 0.002 hr-sq.ft.-° F./British Thermal Unit to produce a non-fouling crude oil feed stock and refining the non-fouling crude oil feed stock in a petroleum refinery to produce at least one liquid transportation fuel.

3. The process of claim 1, wherein the spectroscopy method comprises near-infrared spectroscopy in the range from 3100 cm$^{-1}$ to 6000 cm$^{-1}$.

4. The process of claim 1, wherein the spectroscopy method comprises nuclear magnetic resonance spectroscopy method selected from $^1$H nuclear magnetic resonance spectroscopy and $^{13}$C nuclear magnetic resonance spectroscopy.

5. The process of claim 1, wherein the mother wavelet is selected from the Symlet4 and Symlet6 mother wavelets.

6. The process of claim 1, wherein the mother wavelet is applied at the fourth level of decomposition.

7. The process of claim 1, wherein the mother wavelet is applied at the fifth level of decomposition.

8. The process of claim 1, additionally comprising curating the potential data features of b) to produce a subset of potential data features that are utilized by the trained genetic algorithm to perform the classifying of c).

9. The process of claim 1, wherein the spectral data comprises from 50 to 5000 discrete digitized data points.

10. The process of claim 1, wherein the training of part b) comprises training support vector machines rather than a genetic algorithm to produce trained support vector machines.

11. The process of claim 10, wherein the classifying of c) comprises presenting the sample wavelets coefficients data of a) to the trained support vector machines.

\* \* \* \* \*